United States Patent [19]
Yang

[11] Patent Number: 6,002,055
[45] Date of Patent: Dec. 14, 1999

[54] PROCESS FOR MAKING DIHALODIFLUOROMETHANES AND THEIR HOMOLOGUES

[75] Inventor: Zhen-Yu Yang, Wilmington, Del.

[73] Assignee: E. I. du Pont de Nemours and Company, Wilmington, Del.

[21] Appl. No.: 09/125,465

[22] PCT Filed: Feb. 6, 1997

[86] PCT No.: PCT/US97/01584

§ 371 Date: Aug. 19, 1998

§ 102(e) Date: Aug. 19, 1998

[87] PCT Pub. No.: WO97/30957

PCT Pub. Date: Aug. 28, 1997

Related U.S. Application Data

[60] Provisional application No. 60/012,160, Feb. 23, 1996.
[51] Int. Cl.[6] ............................. C07C 21/18; C07C 51/58
[52] U.S. Cl. ............................................. 570/142; 562/851
[58] Field of Search .............................. 570/142; 562/851

[56] References Cited

U.S. PATENT DOCUMENTS 4,243,770  1/1981  Tatemoto et al. .
4,361,678  11/1982  Tatemoto et al. .

OTHER PUBLICATIONS

Database WPI, Section Ch, Week 9411, Derwent Publications Ltd., 1993.
Z. Yang et al., *Journal of the American Chemical Society*, 117, No. 19, Apr. 17, 1995.
E. O. John et al., *Inorg. Chem.*, 31, 329–331, 1992.
R. A. Mitsh, *J. Heterocyl. Chem.*, 1, 233, 1964.
Z. Yang, *J. Am. Chem. Soc.*, 118, 8140–8141, 1996.

*Primary Examiner*—Alan Siegel

[57] ABSTRACT

Highly fluorinated epoxides are reacted with dihalogens in the presence of metal and metal containing reaction promoters to give dihalofluoromethanes and their homologues.

10 Claims, No Drawings

PROCESS FOR MAKING DIHALODIFLUOROMETHANES AND THEIR HOMOLOGUES

This application claims benefit of provisional application 60/012,160 filed Feb. 23, 1996.

FIELD OF THE INVENTION

This invention pertains to a process for making dihalodifluoromethanes and their homologues by reacting fluorinated epoxides and dihalogen compounds in the presence of selected metal and metal-containing promoters at elevated reaction temperatures.

TECHNICAL BACKGROUND

Dihaloperfluoroalkanes, which may be represented by $X(CF_2)_nY$, where n is 1 to 7, are useful for making functional fluoromonomers and other useful organofluoromaterials. The diiodoperfluoroalkanes are also useful as chain transfer reagents for fluoroelastomers and in the free radical polymerization of fluorinated vinyl monomers. See for example U.S. Pat. Nos. 4,243,770 and 4,361,678, which are incorporated herein by reference.

$CF_2I_2$ is a useful starting material for making organofluoromaterials and as a chain transfer agent for fluoroelastomers, but preparation methods have been shown to have low yields. The reaction of hexafluorocyclopropylene oxide (HFPO) with iodine in a stainless steel vessel has been reported (see John, E. O., et al., Inorg. Chem. 1992, 31, pp. 329–331) but the yield was reported to be 15–30%. Reaction of difluorocarbene with iodine gives less than a 20% yield of $CF_2I_2$ as reported by Mitsh, R. A. J., Heterocyl. Chem. 1964, I, p. 233, and others.

SU-A- 1 297 411 teaches a preparation of difluorodibromomethane by reaction of bromine with hexafluoropropylene oxide, without catalyst.

SUMMARY OF THE INVENTION

This invention pertains to a process for making α,ω-dihaloperfluoromethanes and their homologues, comprising:

reacting a fluorinated epoxide with a dihalogen in the presence of a metal or metal-containing promoter according to Equation I, wherein said promoter is selected from the group consisting of Ni, CuI, Ni/Cu, and Ni/Zn:

(I)

$CF_2XY + X(CF_2)_nY + R_FCOF$ wherein RF represents a perfluoroalkyl or a perfluoroalkyl with one or more ether oxygen, chlorine, bromine, iodine, hydrogen, sulfonyl fluoride, nitrile, ester, acyl chloride or acyl fluoride substituent;

wherein X and Y are each independently selected from the group consisting of I, Br, and Cl;

wherein n is 2 to 6;

and that said dihaloperfluoroalkanes are recovered with a yield of about 70 weight percent or greater.

DETAILS OF THE INVENTION

This invention is an improvement to a process for making dihalodifluoromethanes, generally represented as $CF_2XY$, and their higher homologues, generally represented as $X(CF_2)_nY$ (X,Y=I, Br, Cl; n=2, 3 or 4), and fluorinated acyl fluorides from fluorinated epoxides and dihalogens. The general process may be shown by Equation (I) as follows:

(I)

$CF_2XY + X(CF_2)_nY + R_FCOF$

When this reaction takes place in the presence of the catalyst, a yield of about 70 weight percent or greater, preferably about 80 weight percent or greater, of the desired $CF_2XY$ is often obtained. In the absence of catalyst, the yield is often closer to about 30 weight percent or less of the desired product. $R_F$ in Equation I represents a perfluoroalkyl or a perfluoroalkyl with one or more ether oxygen, chlorine, bromine, iodine, hydrogen, sulfonyl fluoride, nitrile, ester, acyl chloride or acyl fluoride substituents, and serves to define the fluorinated epoxides useful in this invention.

The improvement in the aforementioned process is the presence of a selected metal or metal-containing promoter. As used herein, a "metal or metal-containing promoter" is comprised of a zero-valent metal (e.g., Ni, Cu) or combination of metals (i.e., Ni/Cu, Ni/Zn) or a metal halide (e.g., CuI), usually in the form of a powder or slurry. Alternatively the "metal or metal containing promoter" may be a metal or combination of metals, which form a process vessel (e.g., tube, tank, autoclave, reactor), so that the vessel's surface promotes the reaction. Examples of preferred vessel materials include nickel alloy materials such as Hastelloy® C (Union Carbide, Danbury, Conn.). As found in the Metals Handbook, American Society for Metals, Metals Park, Ohio 44073, 1985, p. 20.28, Hastelloy® C is comprised of about 56% Ni. Therefore, as stated herein, the "presence of" a promoter means that the reactants are exposed to the metal or metal-containing promoter, either by mixing the reactants with a particulate or slurry form of the promoter, or by contact with a container or process vessel which contains the promoting material. It is preferred if the promoter metal comprises at least about 20 to 25% of the slurry or of the process vessel. Yield decreases substantially where the promoter is absent or deficient. For example, if the process takes place in a vessel other than one comprised of a nickel alloy (and in the absence of any added promoter powder or slurry) a maximum of about 30% yield is obtained. To determine if a vessel or other material may have promoting capabilities, a test reaction can be run in the presence of a coupon or in a vessel made of the material in question, which would require minimum experimentation. An example of a typical vessel material which does not show promoting capabitility is stainless steel 316, which is comprising of only 10–14% Ni. See Metals Handbook, American Society of Metals, Metals Park, Ohio 44073, 1985, p. 15.3. This is consistent with the disclosure summarized in Inorg. Chem., 31(2), 1994, pp. 329–331 as cited above.

In a preferred embodiment of the invention, a vessel such as an autoclave is charged with the dihalogen and the fluorinated epoxide material, of which HFPO is preferred, and the mixture is heated for a period of time, generally 8 to 20 hours. If the vessel is not comprised of the catalytic material, then the catalyst is charged to the vessel, with the reactants before mixing and heating. The amount of catalyst added is the lowest effective amount, which has been found to be about 1.5 mole percent. Additional catalyst may be added up to about 20 mole percent to increase the yield to greater than the 50% yield obtained with the 3 mole percent addition. After the reaction is completed, the resulting mixture is then separated into its components, with the preferred separation method being distillation.

By "dihaloperfluoroalkane" is meant a fully-fluorinated alkane which has two halogens, specifically chlorine, bromine and iodine, in place of two fluorines. These halogens are on the terminal ends of the perfluoroalkane. The halogens may be the same or different. By "dihalogen" is meant a compound represented by XY, where X and Y are each independently Cl, Br or I. Non-limiting examples include $I_2$, $Cl_2$, $Br_2$ and ICl.

By "fluorinated acyl fluoride" is meant a compound of the general formula RCOF, wherein R represents fluorinated aliphatic groups or fluorinated aliphatic groups substituted with one or more moieties selected from the group consisting of ether oxygen, chlorine, bromine, iodine, hydrogen, sulfonyl fluoride, nitrile, ester, acyl fluoride and perfluorophenyl. By "product mixture" is meant the combination of the products of a reaction.

When $R_F$=—$CF_3$ and X=Y=I, Br, or Cl in Equation I the reaction is represented by Equation I:

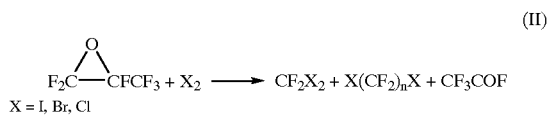

(II)

$$X = I, Br, Cl$$

This reaction therefore yields the preferred compound $CF_2I_2$ when X=I, and n=2, 3, or 4.

Other fluorinated epoxides, where $R_F$ is $CF_2CFClCF_2Cl$, $CF_2OC_6F_5$, or $CF_2OCF_2CF_2SO_2F$, for example, also give $CF_2X_2$ and the corresponding fluorinated acyl fluoride as major products with trace higher homologues (as represented by $X(CF_2)_nX$, N=2, 3, or 4) when reacted with halogens. This is shown in Equation III where X=I, Br or Cl:

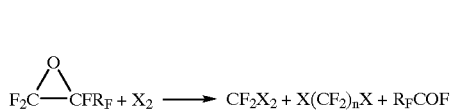

(III)

When excess HFPO or other epoxide is used, the major product of the reaction are the higher homologues, such as $I(CF_2)_3I$, as demonstrated in Example 2.

With interhalogens such as ICl and BrI, a mixture of α,ω-dihalodifluoromethane $CF_2XY$ (X, Y=Cl, Br, I) may be obtained, along with a small amount of $X(CF_2)_nY$ (X, Y=Cl, Br, I; n=2, 3, 4) as shown in Equation IV:

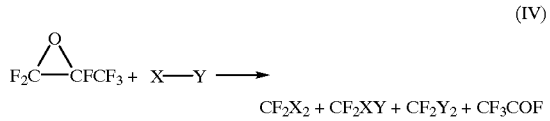

(IV)

Reactions may be carried out in either liquid or gas phase, and either neat (in the absence of solvent) or in solution in inert solvents (e.g., solvents which have no chemical activity on the other materials present). Examples of such solvents include, but are not limited to, chlorofluorocarbons (e.g., $CFC_{113}$), hydrofluorocarbons, perfluoroethers, and perfluorobenzenes. Reaction temperatures are generally about 150° C. to about 300° C., preferably about 180° C. to about 210° C.

In the examples, unless otherwise specified, all reagents were used as received from Aldrich Chemical Co., Milwaukee, Wis. In the following examples, the gas chromatography (GC) was performed on an HP 5890 II Plus gas chromatograph (Hewlett Packard, Wilmington, Del.), using a 20% OV-210 column (Supelco, Bellefonte, Pa.), with an initial temperature of 50° C., a final temperature of 250° C., and a rate of 15° C./min. The $^{19}F$ nuclear magnetic resonance (NMR) data were obtained using a GE Plus NMR spectrometer (General Electric, Schenectady, N.Y.). All measurements are relative to deuterated chloroform ($CDCl_3$). Ratios given are those for peak areas by GC or molar ratios based on NMR data as designated in the specific Examples. High Resolution Mass Spectrometry (HRMS) was done using a Micromass-7070H (VG Analytical, Manchester, UK). GC-MS was also done using the Micromass-7070H.

PREPARATION OF CATALYST

In some of the examples below, freshly made Ni and Ni/Cu catalyst were used. The Ni was prepared according to the following procedure:

To a stirred solution of 133 g of $NiCl_2$ in 1500 mL of water was slowly added 65.0 g of Zn at room temperature. The resultant mixture was stirred for 15 hours. Solids were filtered and poured into 10% HCl and the resulting mixture was stirred for 30 minutes. After filtration, the solids were washed with water, acetone and dried in a vacuum at 60° C. to give 15.5 g Ni.

The Ni/Cu was prepared according to the following procedure:

To a stirred solution of 13.0 g of $NiCl_2$ and 16.0 g of $CuSO_4$ in 100 mL of water was slowly added 13.0 g of Zn at room temperature. Solids were filtrated and poured into 10% HCl and the resulting mixture was stirred for 30 min. After filtration, the solids were washed with water, acetone, and dried in vacuum at 60° C. to give 11.3 g of Ni/Cu catalyst.

ABBREVIATIONS

The following abbreviations are used herein:
bp=boiling point in ° C
s=singlet NMR peak
d=doublet NMR peaks
t=triplet NMR peaks
m=multiplet NMR peaks

EXAMPLES

Example 1

Reaction of HFPO with Iodine in Hastelloy® C Autoclave

A 1-L Hastelloy® C autoclave was charged with 381 g of iodine and then evacuated at low temperature. After 266 g of HFPO was added, the resulting mixture was heated at 185° C. for 10 hours. Subsequently, 184 g of gas was obtained which was mainly $CF_3COF$ determined by $^{19}F$ NMR. Then, 458 g of liquid was washed with aqueous $Na_2SO_3$ solution and brine, and distilled to give a 395 g mixture of $CF_2I_2$, $ICF_2CF_2I$ and $ICF_2CF_2CF_2I$ in a ratio of 240:1:4.8 (GC area), bp 104–106° C. $^{19}F$ NMR for $CF_2I_2$: +18.6 (s); for $ICF_2CF_2I$: −53.3 (s); for $I(CF_2)_3I$: −58.2 (t, J=5 Hz, 4F), −105.3 (m, 2F). HRMS:

calcd. for $CF_2I_2$: 303.8058; for $C_2F_4I_2$: 353.8026; for $C_3F_6I_2$: 403.7994.

Found: for $CF_2I_2$: 303.8002; for $C_2F_4I_2$: 353.7975; for $C_3F_6I_2$: 403.7992.

Example 2

Reaction of Excess HFPO with Iodine in Hastelloy® C Autoclave

A 1-L Hastelloy® C autoclave was charged with 254 g of iodine and then evacuated at low temperature. After 500 g of HFPO was added, the resulting mixture was heated at 185° C. for 30 hours. Then, 350.6 g of gas was obtained which was mainly $CF_3COF$ determiined by $^{19}F$ NMR. GC analysis of 371.4 g of liquid indicated the formation of $CF_2I_2$, $ICF_2CF_2I$, $ICF_2CF_2CF_2I$, $I(CF_2)_4I$ and $I(CF_2)_5I$ in a ratio of 7.1:1:58.7:0.86:0.33 (GC area).

A 1-L Hastelloy® C autoclave was charged with 254 g of iodine and then evacuated at low temperature. After 340 g of HFPO was added, the resulting mixture was heated at 185° C. for 12 hours. GC analysis of 239 g of liquid products indicated the formation of $CF_2I_2$, $ICF_2CF_2I$, $ICF_2CF_2CF_2I$ in a ratio of 90.7:2:6.7 (GC area).

Example 3

Reaction of Hexafluoropropylene Oxide (HFPO) with Iodine in Stainless Steel Shaker Tube A 0.4-L stainless steel shaker tube was charged with 127 g of iodine and then evacuated at low temperature. After 90 g of HFPO was added, the resulting mixture was heated at 185° C. for 8 hours. Then, 71.1 g of iodine was recovered and 23.1 g of liquid was obtained, which was washed with aqueous $Na_2SO_3$ solution and brine and distilled to give 16.9 g of a mixture of $CF_2I_2$, $ICF_2CF_2I$ and $ICF_2CF_2CF_2I$ in a ratio of 95:1:3.3 (mole ratio).

Example 4

Reaction of Hexafluoropropylene Oxide (HFPO) with Iodine in the Presence of Catalyst Ni/Cu in Stainless Steel Shaker Tube A 0.4-L stainless steel shaker tube was charged with 127 g of iodine and 5.0 g of freshly made Ni/Cu and then evacuated at low temperature. After 90 g of HFPO was added, the resulting mixture was heated at 185° C. for 8 hours. Subsequently, 112.0 g of dark liquid was obtained which was distilled to give 79.3 g of a mixture of $CF_2I_2$, $ICF_2CF_2I$ and $ICF_2CF_2CF_2I$ in a ratio of 39.3:1:3 (GC area).

Example 5

Reaction of Hexafluoropropylene Oxide (HFPO) with Iodine in the Presence of Ni in Stainless Steel Shaker Tube A 0.4-L stainless steel shaker tube was charged with 127 g of iodine and 5.0 g of nickel powder (99.99%, 100 mesh, Aldrich Co., Milwaukee, Wis.) and then evacuated at low temperature. After 90 g of HFPO was added, the resulting mixture was heated at 185° C. for 8 hours. An amount of 146.8 g of dark liquid was obtained which was distilled to give 116.8 g of a mixture of $CF_2I_2$, $ICF_2CF_2I$, and $ICF_2CF_2CF_2I$ in a ratio of 64.3:1:4.7 (by GC area).

Example 6

Reaction of Hexafluoropropylene Oxide (HFPO) with Iodine in the Presence of Ni in Stainless Steel Shaker Tube A 0.4-L stainless steel shaker tube was charged with 127 g of iodine and 5.0 g of freshly made Ni powder, and then evacuated at low temperature. After 90 g of HFPO was added, the resulting mixture was heated at 185° C. for 8 hours. An amount of 131.7 g of dark liquid was obtained which was distilled to give 91.6 g of a mixture of $CF_2I_2$, $ICF_2CF_2I$ and $ICF_2CF_2CF_2I$ in a ratio of 14.1:1:1.1 (by GC area).

Example 7

Reaction of Hexafluoropropylene Oxide (HFPO) with Iodine in the Presence of Ni and Cu in Stainless Steel Shaker Tube A 0.4-L stainless steel shaker tube was charged with 127 g of iodine, 2.0 g of freshly made Ni powder and 3.0 g of Cu powder, and then evacuated at low temperature. After 90 g of HFPO was added, the resulting mixture was heated at 185° C. for 8 hours. An amount of 120.1 g of dark liquid was obtained which was distilled to give 91.1 g of a mixture of $CF_2I_2$, $ICF_2CF_2I$ and $ICF_2CF_2CF_2I$ in a ratio of 18.8:1.2:1 (by GC area).

Example 8

Reaction of Hexafluoropropylene Oxide (HFPO) with Iodine in the Presence of Ni and Zn in Stainless Steel Shaker Tube A 0.4-L stainless steel shaker tube was charged with 127 g of iodine, 2.0 g of freshly made Ni powder and 3.0 g of Zn powder and then evacuated at low temperature. After 90 g of HFPO was added, the resulting mixture was heated at 185° C. for 8 hours. An amount of 120.0 g of dark liquid was obtained which was distilled to give 78.4 g of a mixture of $CF_2I_2$, $ICF_2CF_2I$, $ICF_2CF_2CF_2I$ and $I(CF_2)_4I$ in a ratio of 16.1:1.0:1.1:0.2 (by GC area).

Example 9

Reaction of Hexafluoropropylene Oxide (HFPO) with Iodine in the Presence of CuI in Stainless Steel Shaker Tube A 0.4-L stainless steel shaker tube was charged with 127 g of iodine and 10 g of CuI and then evacuated at low temperature. After 90 g of HFPO was added, the mixture was heated at 185° C. for 8 hours. An amount of 126.9 g of mixture was obtained which was distilled to give 103.6 g of a mixture of $CF_2I_2$, $ICF_2CF_2I$ and $ICF_2CF_2CF_2I$ in a ratio of 51.9:1.0:2.5 (by GC area).

Example 10

Reaction of Hexafluoropropylene Oxide (HFPO) with Iodine in Glass Tube

A 50-mL glass tube was charged with 3.8 g of iodine and then evacuated at low temperature. After 1.66 g of HFPO was added, the tube was sealed and the resulting mixture was heated at 185° C. for 20 hours. Liquid was washed with aqueous $Na_2SO_3$ solution and brine to give 1.0 g of black material. $^{19}F$ NMR analysis indicated a mixture of $CF_2I_2$, $ICF_2CF_2I$ and $ICF_2CF_2CF_2I$ in a ratio of 11.2:0.38:1 (mole).

Example 11

Reaction of Excess Hexafluoropropylene Oxide (HFPO) with Iodine in Glass

A 50-mL glass tube was charged with 2.5 g of iodine and then evacuated at low temperature. After 2.8 g of HFPO was added, the tube was sealed and the resulting mixture was heated at 185° C. for 20 hours. Liquid was washed with aqueous $Na_2SO_3$ solution and brine to give 1.1 g of black material which was distilled to give 0.6 g liquid, bp 100 to 123° C. $^{19}F$ NMR analysis indicated a mixture of $CF_2I_2$, $ICF_2CF_2I$ and $ICF_2CF_2CF_2I$ in a ratio of 15:1:20 (mole).

Example 12

Reaction of Hexafluoropropylene Oxide (HFPO) with Iodine in 1,1,2-Trifluorotrichloroethane ($CFC_{113}$) in Hastelloy® C Autoclave A 1-L Hastelloy® C autoclave was charged with 254 g of iodine and 150 mL of $CFC_{113}$, then evacuated at low temperature. After 175 g of HFPO was added, the resulting mixture was heated at 186° C. for 10 hours. An amount of 81.1 g of iodine was recovered and GC analysis indicated that the liquid was a mixture of $CF_2I_2$, $ICF_2CF_2I$ and $ICF_2CF_2CF_2I$ in a ratio of 49.2:1:1.35 (area), which was washed with aqueous $Na_2SO_3$ solution and brine and distilled to give 182.5 g of $CF_2I_2$, bp 103–104° C.

Example 13

Reaction of Excess Hexafluoropropylene Oxide (HFPO) with Bromine in Hastelloy® C Shaker Tube A 0.4-L Hastelloy® C shaker tube was charged with 80 g of bromine and then evacuated at low temperature. After 90 g of HFPO was added, the resulting mixture was heated at 200° C. for 6 hours. Then, 91.3 g of liquid was obtained, which was washed with aqueous $Na_2SO_3$ solution and brine and distilled to give 71.3 g of $CF_2Br_2$, bp 23–25° C. $^{19}F$ NMR: +6.5 (s).

Example 14

Reaction of Excess Hexafluoropropylene Oxide (HFPO) with Bromine in Hastelloy® C Shaker Tube A 0.4-L Hastelloy® C shaker tube was charged with 80 g of bromine and then evacuated at low temperature. After 170 g of HFPO was added, the resulting mixture was heated at 185° C. for 12 hours. $^{19}F$ NMR analysis of 84 g of liquid indicated a mixture of $CF_2Br_2$, $BrCF_2CF_2Br$ and $BrCF_2CF_2CF_2Br$ in a ratio of 56.3::3.3 (mole). Distillation gave 68.5 g of 95% pure $CF_2Br_2$, bp 23–27° C. $^{19}F$ NMR: +6.5 (s).

Example 15

Reaction of Excess Hexafluoropropylene Oxide (HFPO) with Iodine Monochloride in Hastelloy® C Shaker Tube A 0.4-L Hastelloy® C shaker tube was charged with 114 g of iodine monochloride and then evacuated at low temperature. After 120 g of HFPO was added, the resulting mixture was heated at 185° C. for 8 hours. Then, 112.3 g of crude liquid products were obtained, which were distilled to give 14.7 g of $CF_2ICl$, bp 31–34° C., 61.7 g of $CF_2I_2$, bp 103–104° C. $^{19}F$ NMR for $CF_2ICl$: +8.2 (s). HRMS: calcd. for $CF_2ICl$: 311.8637. Found: 311.8678. Trace of $ClCF_2CF_2CF_2I$ was also observed by GC-MS.

Example 16

Reaction of Excess Hexafluoropropylene Oxide (HFPO) with Iodine Monobromide in Hastelloy® C Shaker Tube A 0.4-L Hastelloy® C shaker tube was charged with 62 g of iodine monobromide and then evacuated at low tempera-ture. After 58 g of HFPO was added, the resulting mixture was heated at 185° C. for 6 hours. Liquid products were washed with aqueous $Na_2SO_3$ solution and water to give 42.3 g of a mixture of $CF_2I_2$, $CF_2BrI$ and $CF_2Br_2$ in a ratio of 1.7:1:2.5 and small amounts of $Br(CF_2)_3Br$, $ICF_2CF_2I$ and $ICF_2CF_2CF_2I$ detected by GC-MS. $^{19}F$ NMR for $CF_2BrI$: +13.6. HRMS: calcd. for $CF_2BrI$: 255.8196. Found: 255.8103.

Example 17

Reaction of $C_6F_5OCF_2CFOCF_2$ with Iodine in Glass Tube

A 25-mL glass tube was charged with 2.54 g of iodine and 3.3 g of $C_6F_5OCF_2CFOCF_2$ and then evacuated at low temperature. After the tube was sealed, the resulting mixture was heated at 200° C. for 8 hours. 4.2 g liquid products were transferred into a −78° C. trap. $^{19}F$ NMR analysis indicated that the liquid was 40.8% (mole) of $CF_2I_2$, 51.2% of $C_6F_5CF_2OCF_2COF$, 7.6% of $I(CF_2)_3I$ and 0.8% of $ICF_2CF_2I$. $^{19}F$ NMR for $C_6F_5OCF_2COF$: +16.7 (t, J=2.4 Hz, 1F), −77.3 (m, 2F), −151.2 (m, 2F), −154.2 (t, J=22 Hz, 1F), −160.8 (m, 2F). HRMS: calcd. for $C_8F_8O_2$: 279.9771. Found: 279.9719.

Example 18

Reaction of $C_6F_5OCF_2CFOCF_2$ with Bromine in Glass Tube

A 25-mL glass tube was charged with 0.8 g of bromine and 1.7 g of $C_6F_5OCF_2CFOCF_2$ and then evacuated at low temperature. After the tube was sealed, the resulting mixture was heated at 200° C. for 20 hours. 2.0 g crude liquid products were obtained. $^{19}F$ NMR analysis indicated that the liquid was a mixture of $C_6F_5CF_2OCF_2COF$, $CF_2Br_2$, $BrCF_2CF_2Br$ and $BrCF_2CF_2CF_2Br$ in a ratio of 28.7:15.3:5.7:1 (mole).

Example 19

Reaction of $CF_2ClCFClCF_2CFOCF_2$ with Iodine in Glass Tube

A 25-mL glass tube was charged with 3.5 g of iodine and 4.1 g of $CF_2ClCFClCF_2CFOCF_2$ and then evacuated at low temperature. After the tube was sealed, the resulting mixture was heated at 190° C. for 8 hours and 200° C. for 12 hours. Then, 4.3 g liquid products with small amounts of iodine were transferred into a −78° C. trap. $^{19}F$ NMR analysis indicated that the liquid was 34% $CF_2I_2$, 62.5% $CF_2ClCFClCF_2OCF_2COF$, 3.4% $I(CF_2)_3I$ and 0.8% $ICF_2CF_2I$ (mole ratio). $^{19}F$ NMR for $CF_2ClCFClCF_2COF$: +26.2 (t, J=2.4 Hz, 1F), −63.5 (dm, J=175 Hz, F), −64.7 (dm, J=175 Hz, 1F), −110.4 (dm, J=270.3 Hz, 1F), −113.2 (dm, J=270.2 Hz, 1F), −131.4 (m, 1F). HRMS: calcd. for $C_4F_6Cl_2O$—$COF$: 200.9297. Found: 200.9257.

Example 20

Reaction of $CF_2ClCFClCF_2CFOCF_2$ with Bromine in Glass Tube

A 25-mL glass tube was charged with 0.8 g of bromine and 1.5 g of $CF_2ClCFClCF_2CFOCF_2$ and then evacuated at low temperature. After the tube was sealed, the resulting mixture was heated at 200° C. for 10 hours. Subsequently, 2.3 g crude products were obtained. $^{19}F$ NMR analysis indicated that the conversion was 85% and a 1:1 mixture of $CF_2Br_2$ and $CF_2ClCFClCF_2COF$ was formed.

Example 21

Reaction of $FO_2SCF_2CF_2OCF_2CFOCF_2$ with Iodine in Glass Tube

A 25-mL glass tube was charged with 3.5 g of iodine and 4.1 g of $CF_2ClCFClCF_2CFOCF_2$ and then evacuated at low temperature. After the tube was sealed, the resulting mixture was heated at 200° C. for 8 hours. Then. 2.8 g of the liquid products with small amounts of iodine were transferred into a −78° C. trap. $^{19}F$ NMR analysis indicated that the liquid was 34% (mol) $CF_2I_2$, 62.5% $FO_2SCF_2CF_2OCF_2COF$, 3.4% $I(CF_2)_3I$ and 0.8% $ICF_2CF_2I$. $^{19}F$ NMR for $FO_2SCF_2CF_2OCF_2COF$: +45.6 (m, 1F), +14.9 (s, 1F), −76.7 (t, J=11.7 Hz, 2F), −82.1 (m, 2F), −112.5 (m, 2F). HRMS: calcd. for $C_4F_8SO_4$—COF: 248.9456. Found: 248.9468.

What is claimed is:

1. A process for making dihaloperfluoromethanes and their homologues, comprising:

reacting a fluorinated epoxide with a dihalogen in the presence of a metal or metal-containing promoter according to Equation I, wherein said promoter is selected from the group consisting of Ni, CuI, Ni/Cu, and Ni/Zn:

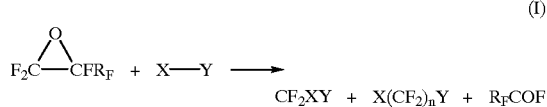

$$CF_2XY + X(CF_2)_nY + R_FCOF$$

wherein RF represents a perfluoroalkyl or a perfluoroalkyl with one or more ether oxygen, chlorine, bromine, iodine, hydrogen, sulfonyl fluoride, nitrile, ester, acyl chloride or acyl fluoride substituent;

wherein X and Y are each independently selected from the group consisting of I, Br, and Cl;

wherein n is 2 to 6;

and provided that said dihaloperfluoroalkanes are recovered with a yield of at least about 70 weight percent.

2. The process as recited in claim 1 wherein said fluorinated epoxide is hexafluoropropylene oxide.

3. The process as recited in claim 1 wherein at least about 3 mole percent of said metal or metal containing promoter is used.

4. The process as recited in claim 1 wherein said promoter is present in the form of a metal or metal-containing powder or slurry.

5. The process as recited in claim 1 wherein said promoter is present in the form of a process vessel.

6. The process as recited in claim 1 wherein said reaction occurs in the presence of an inert solvent.

7. The process as recited in claim 1 wherein said reaction occurs in the absence of solvent.

8. The process as recited in claim 1 wherein said yield is at least about 80 weight percent.

9. The process as recited in claim 1 wherein said reaction temperature is between about 150° C. and about 300° C.

10. The process of claim 1 wherein the promoter metal comprises at least 20% of a slurry form of the promoter or of a process vessel formed from metal or metal containing promoter.

* * * * *